United States Patent
Kim et al.

(10) Patent No.: US 10,234,403 B2
(45) Date of Patent: Mar. 19, 2019

(54) DEVICE AND METHOD OF OPTICAL INSPECTION ON CARBON FIBER REINFORCED PLASTICS COMPONENTS

(71) Applicant: KOREA INSTITUTE OF INDUSTRIAL TECHNOLOGY, Cheonan-si, Chungcheongnam-do (KR)

(72) Inventors: Hyo Young Kim, Anseong-si (KR); Tae Gon Kim, Cheonan-si (KR); Seok Woo Lee, Seongnam-si (KR)

(73) Assignee: Korea Institute of Industrial Technology, Cheonan-si, Chungcheongnam-do (KR)

( * ) Notice: Subject to any disclaimer, the term of this patent is extended or adjusted under 35 U.S.C. 154(b) by 0 days.

(21) Appl. No.: 15/114,609

(22) PCT Filed: May 20, 2016

(86) PCT No.: PCT/KR2016/005409
§ 371 (c)(1),
(2) Date: Jul. 27, 2016

(87) PCT Pub. No.: WO2016/195299
PCT Pub. Date: Dec. 8, 2016

(65) Prior Publication Data
US 2017/0146464 A1 May 25, 2017

(30) Foreign Application Priority Data
Jun. 2, 2015 (KR) .................. 10-2015-0078205

(51) Int. Cl.
*G06T 7/50* (2017.01)
*G01N 21/95* (2006.01)
(Continued)

(52) U.S. Cl.
CPC ......... *G01N 21/9515* (2013.01); *G01N 21/88* (2013.01); *G01N 21/93* (2013.01);
(Continued)

(58) Field of Classification Search
CPC ............... G01N 21/9515; G01N 21/93; G01N 2021/9518; G06T 7/50; G06K 9/4661;
(Continued)

(56) References Cited

U.S. PATENT DOCUMENTS 5,963,328 A * 10/1999 Yoshida ............. G01N 21/8806
356/237.2
8,172,242 B1 * 5/2012 Crandall .............. A61B 5/0059
280/47.35
(Continued)

FOREIGN PATENT DOCUMENTS

KR  1000590660000     2/1993
KR  1007431520000 B1  7/2007
(Continued)

*Primary Examiner* — William C Vaughn, Jr.
*Assistant Examiner* — Jae N Noh
(74) *Attorney, Agent, or Firm* — Rabin & Berdo, P.C.

(57) ABSTRACT

An embodiment of the present disclosure, provides a method of optical inspection on a carbon fiber reinforced plastics (CFRP) component in which performs an inspection, by maintaining the focal distance for a surface of an object to be inspected, and making a light axis of an image device and a normal line of the surface of the object to be inspected to be identical.

7 Claims, 4 Drawing Sheets

(51) Int. Cl.
    *G01N 21/88*     (2006.01)
    *G01N 21/93*     (2006.01)
    *G06K 9/46*     (2006.01)
    *H04N 5/232*     (2006.01)
    *H04N 5/907*     (2006.01)
    *G06K 9/20*     (2006.01)
    *H04N 5/77*     (2006.01)

(52) U.S. Cl.
    CPC ............. *G01N 21/95* (2013.01); *G06K 9/209* (2013.01); *G06K 9/4661* (2013.01); *G06T 7/50* (2017.01); *H04N 5/232* (2013.01); *H04N 5/23212* (2013.01); *H04N 5/23216* (2013.01); *H04N 5/907* (2013.01); *G01N 2021/9518* (2013.01); *H04N 5/77* (2013.01)

(58) Field of Classification Search
    CPC . H04N 5/23212; H04N 5/23216; H04N 5/907
    USPC ........................................ 375/240.16; 348/95
    See application file for complete search history.

(56) References Cited

U.S. PATENT DOCUMENTS

| 9,756,297 | B1* | 9/2017 | Clements | ............... H04N 7/185 |
| 2010/0208061 | A1* | 8/2010 | Lee | .................... G01N 21/6452 |
| | | | | 348/135 |
| 2011/0106313 | A1* | 5/2011 | Lee | .......................... B25J 5/007 |
| | | | | 700/259 |
| 2012/0218405 | A1* | 8/2012 | Terreno | .............. G01N 21/9515 |
| | | | | 348/125 |

FOREIGN PATENT DOCUMENTS

| KR | 1014522150000 B1 | 10/2014 |
| KR | 1014910490000 | 2/2015 |

* cited by examiner

DEVICE AND METHOD OF OPTICAL INSPECTION ON CARBON FIBER REINFORCED PLASTICS COMPONENTS

CROSS REFERENCE TO RELATED APPLICATIONS

This application is the U.S. National Phase of International Application No. PCT/KR2016/005409, filed May 20, 2016, which claims the benefit of Korean Patent Application No. 10-2015-78205, filed Jun. 2, 2015. Any and all applications for which a foreign or domestic priority claim is identified here or in the Application Data Sheet as filed with the present application are hereby incorporated by reference in their entireties under 37 CFR 1.57.

TECHNICAL FIELD

The present disclosure relates to a method of optical inspection on products of a carbon fiber reinforced plastics material, more particularly the method of optical inspection which is performed in high speed and in high precision on a surface formed with an interior and exterior curved surface of products made of CFRP (carbon fiber reinforced plastic) material.

BACKGROUND ART

When an optical inspection is generally performed on an object to be inspected, an image device of a device of optical inspection requires a complicated operation in order to minimize an inspection error of a surface of shape formed with a curved surface. To be a reference for a complicated operation, is an image captured angle of the image device which corresponds to an incident angle and a reflected angle of light source with a normal line of the curved surface and a distance between a lens of the image device and the curved surface.

When the object to be inspected is a plane, an optical inspection may be performed while constantly maintaining the initially determined image captured angle of the image device and the distance between the lens and the surface of the image device. However, when the object to be inspected is a curved surface, the distance between the lens of the image device and the surface and the direction of the normal line of the curved surface are persistently changed depending on the test position. Therefore, in the inspection for a curved surface, it is important to constantly maintain the image captured angle of the image device for the normal line of a curve surface and the distance between the lens and the surface of the image device.

CFRP is an abbreviation of Carbon Fiber Reinforced Plastics, and a carbon fiber reinforced plastics (CFRP) material is a composite material made of a plurality of carbon fiber and a plurality of thermosetting resin. Since various shapes of products may be produced due to a property of carbon fiber reinforced plastics (CFRP) material, products made of the carbon fiber reinforced plastics (CFRP) may comprise a shape composed of a curved surface of which a curved ratio is large. Also, it has been increased that the carbon fiber reinforced plastics (CFRP) material is used for a large size product.

Therefore, the device of optical inspection is required to perform a precise inspection for a surface of which a curved ratio is large, while it is required to perform a high speed inspection for a large sized surface.

SUMMARY OF INVENTION

The technical problem solved by the present disclosure is to provide a method of optical inspection on a carbon fiber reinforced plastics (CFRP) component which is performed in high speed and in high precision by constantly maintaining a distance between the lens and the curved surface of the image device and changing an image captured angle of the image device depending on the direction of the normal line of the curved surface such that a normal line of the curved surface is to be identical to a light axis of the image device when performing optical inspection on a curved surface of a product manufactured with a carbon fiber reinforced plastics (CFRP) material.

The present disclosure conceived to achieve the above mentioned technical problem, in a method of optical inspection on a carbon fiber reinforced plastics (CFRP) component, provides the method of optical inspection of the carbon fiber reinforced plastics (CFRP) component, characterized in comprising a step of collecting shape data of a surface of an object to be inspected; calculating a distance between the surface of the object to be inspected and an image device based on the shape data of the surface of the object to be inspected, and calculating an angle between a light axis of the image device and a normal line of the surface of the object to be inspected; moving the image device such that a distance between the surface of the object to be inspected and the image device is identical to the focal distance of the image device; and adjusting an angle of the image device such that the light axis of the image device is identical to the normal line of the surface of the object to be inspected. The above mentioned configuration has an effect capable of readily performing the optical inspection in high speed and in high precision, by making it to be performed simultaneously for maintaining a distance between a lens of an image device and a curved surface and matching between a normal line of the curved surface and a light axis of the image device.

Advantageous Effects of Invention

In accordance with an embodiment of the present disclosure, since an inspection is preceded as a distance between an image device and a surface of an object to be inspected keeps to be constantly maintained, an inspection material with the same level of sharpness may be collected.

Further, in accordance with an embodiment of the present invention, by changing an image captured angle depending on a direction of the normal line of a curve surface such that a normal line of the curved surface is to be identical to a light axis of the image device and thus an inspection error may be minimized.

Further in accordance with an embodiment of the present invention, both maintaining a distance between a lens of the image device and the curved surface and making the normal line of the curved surface and the light axis of the image device to be identical are simultaneously performed, and thus an optical inspection is readily available in high speed and in high precision.

The effects of the present disclosure is not limited to the above mentioned effects, and should be understood that whole effects inferable from a configuration thereof which is written in a description and claims thereof are included.

DESCRIPTION OF EMBODIMENTS

Figure 1:
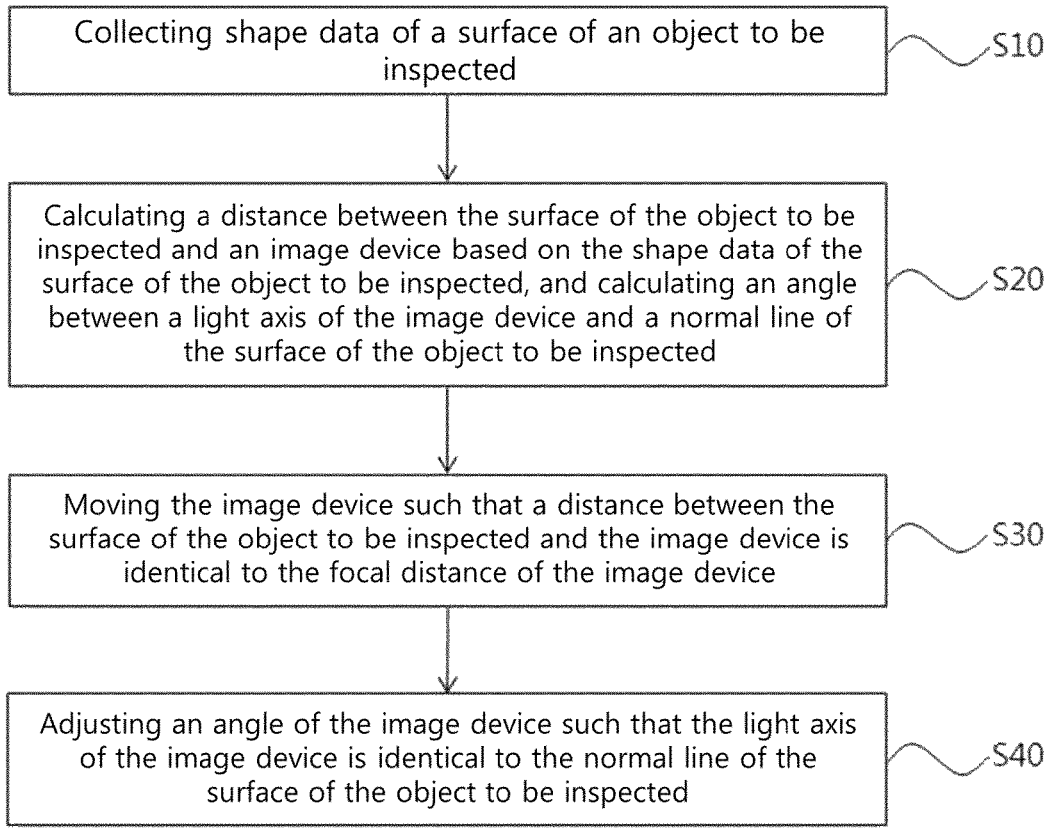
FIG. 1 is a flow diagram of a method of optical inspection on a carbon fiber reinforced plastics (CFRP) component, in accordance with an embodiment of the present disclosure.

To achieve the technical problem, an embodiment of the present disclosure provides the method of optical inspection on the carbon fiber reinforced plastics (CFRP) component, characterized in comprising a step of (a) collecting shape data of a surface of an object to be inspected; (b) calculating a distance between the surface of the object to be inspected and an image device based on the shape data of the surface of the object to be inspected, and calculating an angle between a light axis of the image device and a normal line of the surface of the object to be inspected; (c) moving the image device such that a distance between the surface of the object to be inspected and the image device is identical to the focal distance of the image device; and (d) adjusting an angle of the image device such that the light axis of the image device is identical to the normal line of the surface of the object to be inspected.

In an embodiment of the present disclosure, the step of (a) may be performed for the shape data of the surface of the object to be inspected toward to the image device to be collected.

In an embodiment of the present disclosure, the step of (b) may be performed for a vertical distance from the image device to the surface of the object to be inspected to be calculated, by setting at least three reference points for the shape data of the object to be inspected.

In an embodiment of the present disclosure, the step of (b) may be performed for an angle where the light axis of the image device is identical to the normal line of the surface of the object to be inspected to be calculated, by setting at least three reference points for the shape data of the object to be inspected.

In an embodiment of the present disclosure, the step of (c) may be performed for the image device to reciprocate in vertical direction.

In an embodiment of the present disclosure, the step of (d) may be performed for the image device to be operated in swing motion.

In an embodiment of the present disclosure, the step of (c) and (d) may be simultaneously performed.

To achieve the technical problem, an embodiment of the present disclosure provides a device of optical inspection on a carbon fiber reinforced plastics (CFRP) component, comprising an image device configured to perform an inspection on a surface of an object to be inspected; a data processor configured to collect shape data of the surface of the object to be inspected, calculate a distance between the surface of the object to be inspected and an image device based on the shape data of the surface of the object to be inspected, and calculate an angle between a light axis of the image device and a normal line of the surface of the object to be inspected; a first operating unit configured to move the image device such that a distance between the surface of the object to be inspected and the image device is identical to the focal distance of the image device; and a second operating unit configured to adjust an angle of the image device such that the light axis of the image device is identical to the normal line of the surface of the object to be inspected.

In an embodiment of the present disclosure, the device of optical inspection on a carbon fiber reinforced plastics (CFRP) component, further comprises a controller configured to generate a control signal based on data calculated at the data processor and transfer the control signal to the first operating unit and to second operating unit.

In an embodiment of the present disclosure, the device of optical inspection on a carbon fiber reinforced plastics (CFRP) component further comprises a memory configured to store inspection data collected by the image device.

In an embodiment of the present disclosure, the data processor may collect the shape data of the surface of the object to be inspected toward to the image device.

In an embodiment of the present disclosure, the data processor may set at least three reference points for the object to be inspected, and calculate a vertical distance from the image device to the surface of the object to be inspected.

In an embodiment of the present disclosure, the data processor may set at least three reference points for the object to be inspected, and calculates an angle where the light axis of the image device is identical to the normal line of the surface of the object to be inspected.

In an embodiment of the present disclosure, the first operating unit may reciprocate the image device in vertical direction.

In an embodiment of the present disclosure, the second operating unit may operate the image device to be in swing motion.

In an embodiment of the present disclosure, the first operating unit and the second operating unit may be simultaneously operated.

Embodiments

Hereinafter, the present disclosure will be explained with reference to the accompanying drawings. However, the present disclosure can be practiced in various ways and is not limited to the embodiments described herein. In the drawings, parts which are not related to the description are omitted to clearly set forth the present disclosure and similar elements are denoted by similar reference symbols throughout the specification.

Throughout the description, when some parts are "connected (interfaced, contacted, combined)" to other parts, this comprises not only a case being "directly connected," but also a case being "indirectly connected" with other member therebetween. Further, when some parts "comprises" some elements, this means not exclude other elements unless otherwise stated, but further capable of comprising other elements.

The terms used in the present disclosure is only used to explain a specific embodiment, and there is no intent to limit the present disclosure. A singular term comprises the plural term, unless clearly otherwise intended. In the present description, the terms "comprises" and "have" and so on should be understood to designate that features, numbers, steps, operations, elements, components or combinations thereof are existed, and not to exclude in advance the possible existence or addition of one or more distinctive features, numbers, steps, operations, elements, components or combinations thereof.

Hereinafter, an embodiment of the present disclosure will be in detail explained with reference to the accompanying drawings.

Figure 2:
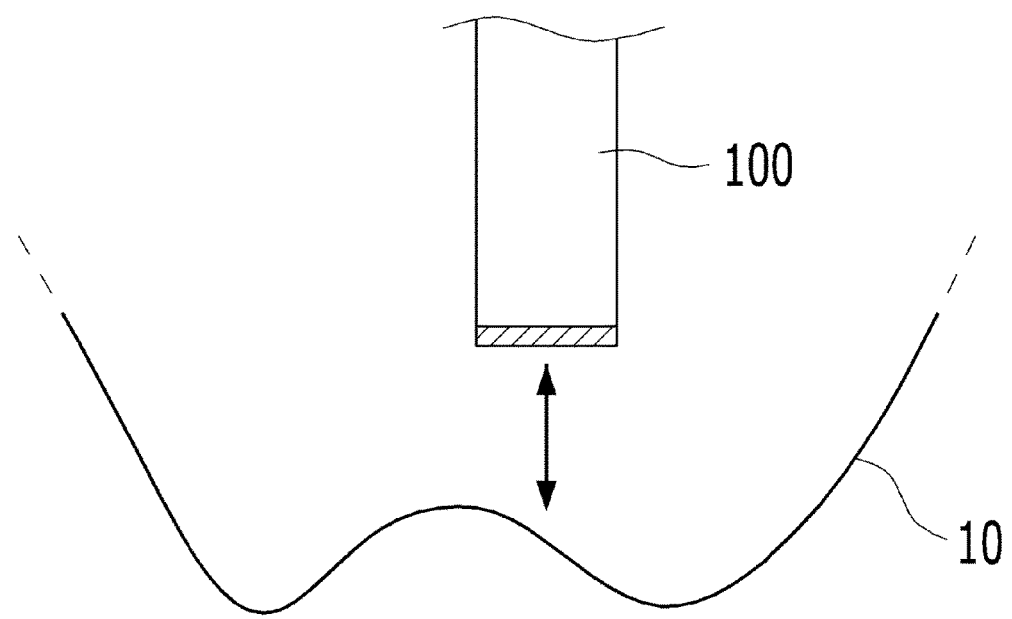
FIG. 2 is an exemplary diagram of a state maintaining a focal distance of the image device, in accordance with an embodiment of the present disclosure.
Figure 3:
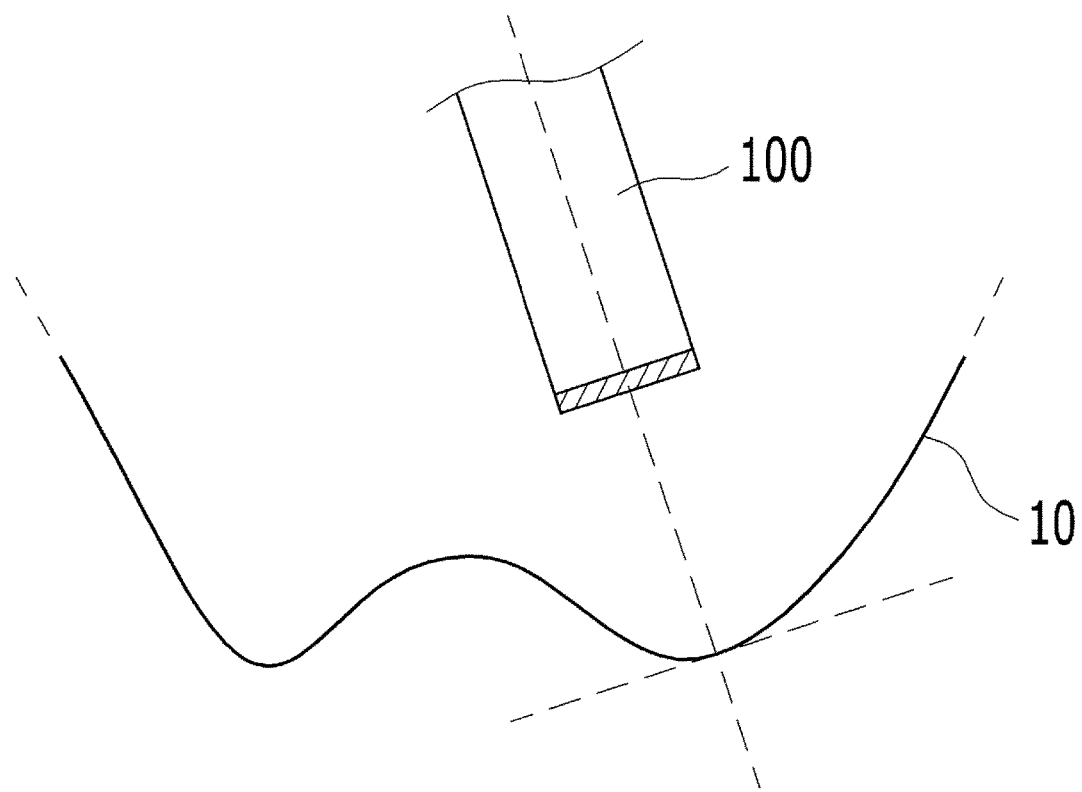
FIG. 3 is an exemplary diagram on a state where a light axis of the image device is identical to a normal line of a surface of an object to be inspected, in accordance with an embodiment of the present disclosure.
Figure 4:
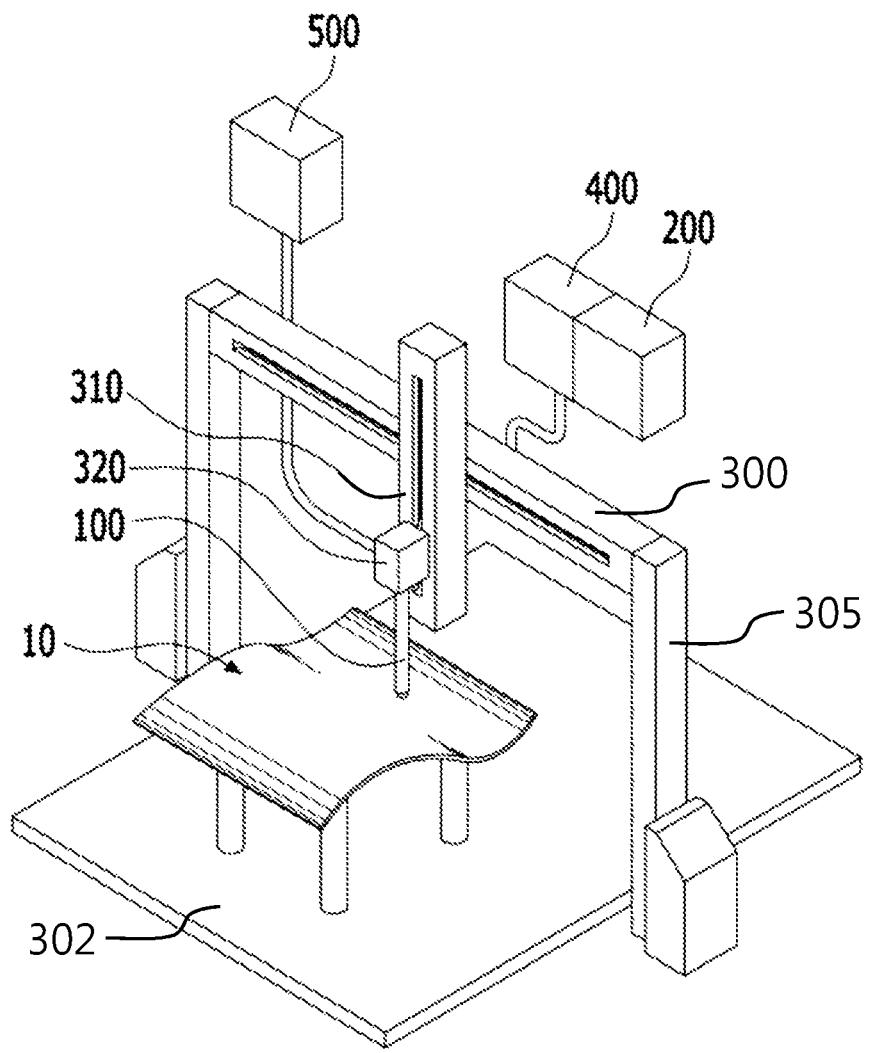
FIG. 4 is a schematic perspective diagram of a device of optical inspection on a carbon fiber reinforced plastics (CFRP) component.

FIG. 1 is a flow diagram of a method of optical inspection on a carbon fiber reinforced plastics (CFRP) component, in accordance with an embodiment of the present disclosure, FIG. 2 is an exemplary diagram of a state maintaining a focal distance of the image device, in accordance with an embodiment of the present disclosure, FIG. 3 is an exemplary diagram on a state where a light axis of the image device is identical to a normal line of a surface of the object to be inspected, in accordance with an embodiment of the present disclosure, and FIG. 4 is a schematic perspective diagram of a device of optical inspection on a carbon fiber reinforced plastics (CFRP) component.

As shown in FIG. 1, a method of optical inspection on a carbon fiber reinforced plastics (CFRP) component, may comprise a step of collecting shape data of a surface of an object to be inspected (S10); calculating a distance between the surface of the object to be inspected and an image device based on the shape data of the surface of the object to be inspected, and calculating an angle between a light axis of the image device and a normal line of the surface of the object to be inspected (S20); moving the image device such that a distance between the surface of the object to be inspected and the image device is identical to the focal distance of the image device (S30); and adjusting an angle of the image device such that the light axis of the image device is identical to the normal line of the surface of the object to be inspected (S40).

In an embodiment of the present invention, it is explained for the step of moving the image device such that a distance between the surface of the object to be inspected and the image device is identical to the focal distance of the image device (S30); and adjusting an angle of the image device such that the light axis of the image device is identical to the normal line of the surface of the object to be inspected (S40), but the step of (S30) and (S40) may be performed as the image device moves from one inspection point to the other inspection point. Herein, the movement from one inspection point to the other inspection point may be a discrete operation or a continuous operation.

Firstly, the step of collecting shape data of the surface of the object to be inspected 10 (S10) may be proceeded.

Herein, shape data of the surface of the object to be inspected 10 toward to an image device 100 may be collected.

Also, the shape data of the surface of the object to be inspected 10 may be calculated and collected using a CAD program.

In an embodiment of the present invention, it is explained that the shape data of the surface of the object to be inspected 10 is calculated and collected using a CAD program, but is not limited to the program and thus a program such as a CATIA or a SOLIDWORKS and so on may be used.

Also, based on the shape data of the surface of the object to be inspected 10, the step of calculating a distance between the surface of the object to be inspected 10 and the image device 100, and calculating an angle between a light axis of the image device 100 and a normal line of the surface of the object to be inspected 10 (S20) may be performed.

Herein, a vertical distance from the image device 100 to the surface of the object to be inspected 10 may be calculated, by setting at least three reference points for the shape data of the object to be inspected 10.

Also, an angle where the light axis of the image device 100 is identical to the normal line of the surface of the object to be inspected 10 may be calculated, by setting at least three reference points for the shape data of the object to be inspected 10.

Herein, in order to maintain three dimensional shapes with a specific location, it is required that at least three reference points are set, and the at least three reference points may be arbitrarily set from the object to be inspected 10, and may be set as a point where the object to be inspected 10 is contacted to a fixed structure.

Further, the step of moving the image device 100 such that a distance between the surface of the object to be inspected 10 and the image device 100 is identical to the focal distance of the image device 100 (S30) may be performed.

Herein, the image device 100 may persistently reciprocate in vertical direction such that distance between the surface of the object to be inspected 10 and the image device 100 is identical to the focal distance of the image device 100.

In this case, three dimensional location information of the image device 100 and the object to be inspected 10 are to be collected in a data processor 200, and the focal distance may be maintained based on the pre-collected location information without any further sensor.

Further, the step of adjusting an angle of the image device 100 such that the light axis of the image device 100 may be identical to the normal line of the surface of the object to be inspected 10 (S40) may be performed.

In this case, the data processor 200 divides the object to be inspected 10 into a small unit of cell, collects information on a normal line at the center of each of cells, which is not information on a normal line for entire points of the surface of the object to be inspected 10, and makes the light axis of the image device 100 to be identical to the normal line at the center of each of cells, and thus may reduce the number of adjusting an angle of the image device 100 and increase an inspection speed.

Herein, an area in the small unit of cell may be adjusted to a level which an inspection error is to be minimized.

Also, the image device 100 adjusts an angle of the image device 100 while it is operated in swinging motion, and thus makes the light axis of the image device 100 to be identical to the normal line of the surface of the object to be inspected 100.

There is an effect capable of collecting inspection data of which sharpness keeps to be constantly maintained, resulted from an inspection at an angle where the light axis of the above mentioned image device 100 is identical to the normal line of the surface of the object to be inspected 10.

Further, the step of moving the image device 100 such that a distance between the surface of the object to be inspected 10 and the image device 100 is identical to the focal distance of the image device 100 (S30) and adjusting an angle of the image device 100 such that the light axis of the image device 100 may be identical to the normal line of the surface of the object to be inspected 10 (S40) may be simultaneously performed.

As shown in FIG. 2, the image device 100 may move as the focal distance of the image device 100 is closely maintained to the surface of the object to be inspected 10.

In this case, as the image device 100 moves, maintaining the focal distance, the movement to a point of which a height is different is performed by a continuous operation without any discrete operation, and thus a high speed inspection is available.

As shown in FIG. 3, an inspection may be performed for an interval where a curved ratio is persistently changed.

In this case, as the light axis of the image device 100 is identical to the normal line of the surface of the object to be inspected 10 and thus an inspection on the surface of the object to be inspected 10 is performed, regardless of a curved ratio, a precise inspection may be performed.

As shown in FIG. 4, a device of optical inspection on a carbon fiber reinforced plastics (CFRP) component, may comprise an image device 100 configured to perform an inspection on a surface of the object to be inspected; a data processor 200 configured to collect shape data of the surface of the object to be inspected 10, calculate a distance between the surface of the object to be inspected 10 and an image device 100 based on the shape data of the surface of the object to be inspected, and calculate an angle between a light axis of the image device 100 and a normal line of the surface of the object to be inspected 10; a base 302 on which the object to be inspected is placed; a horizontal rail 300 extending in a horizontal direction with a predetermined length; two supports 305 separately and vertically installed at both sides of the base 302 and supporting the horizontal rail 300 at both ends of the horizontal rail 300; a first operating unit (or a vertical rail) 310 configured to move in the horizontal direction on the horizontal rail 300 to move the image device 100 such that a distance between the surface of the object to be inspected 10 and the image device 100 is identical to the focal distance of the image device 100; and a second operating unit (or an angle adjusting part) 320 configured to move in the vertical direction on the first operating unit 310 to adjust an angle of the image device 100 such that the light axis of the image device 100 is identical to the normal line of the surface of the object to be inspected 10.

The device of optical inspection on a carbon fiber reinforced plastics (CFRP) component may further comprises a controller 400 configured to generate a control signal based on data calculated at the data processor 200 and transfer the control signal to the first operating unit 310 and to second operating unit 320.

The device of optical inspection on a carbon fiber reinforced plastics (CFRP) component may further comprises a memory 500 configured to store inspection data collected by the image device 100. The data processor 200 may collect the shape data of the surface of the object to be inspected 10 toward to the image device 100.

The data processor 200 may set at least three reference points for the object to be inspected 10, and calculate a vertical distance from the image device 100 to the surface of the object to be inspected 10.

The data processor 200 may set at least three reference points for the object to be inspected 10, and calculate an angle where the light axis of the image device 100 is identical to the normal line of the surface of the object to be inspected 10.

The first operating unit 310 may reciprocate the image device 100 in vertical direction.

The second operating unit 320 may operate the image device 100 to be in swing motion.

The first operating unit 310 and the second operating unit 320 may be simultaneously operated.

The above mentioned explanation of the present disclosure is to illustrate, and those who are skilled in the art of the present disclosure may understand that it is capable of being modified in other specific manner without changing technical spirits or essential features of the present disclosure. Therefore, the above mentioned embodiments are to be illustrative in every way and should be understood not to be limited. For example, each elements explained in a singular form may be implemented in a distributed form, and in similar, each elements explained to be distributed may be implemented in a combined form.

The scope of the present disclosure is represented by following claims, and intentions and scopes of the claims and all changes or modifications drawn from an equivalent concept of the claims should be interpreted to be included therein.

REFERENCE SIGNS LIST

10: object to be inspected
100: image device
200: data processor
310: first operation unit
320: second operation unit
400: controller
500: memory

The invention claimed is:

1. A method for optically inspecting a carbon fiber reinforced plastics (CFRP) component using a device including:
   a base;
   two supports separately and vertically installed at both sides of the base;
   a horizontal rail extending in a horizontal direction with a predetermined length, wherein both ends of the horizontal rail are supported by the supports;
   a vertical rail extending in a vertical direction with a predetermined length and moving in the horizontal direction along the horizontal rail;
   an angle adjusting head moving in the vertical direction along the vertical rail and being operated in swing motion;
   an image device mounted on the angle adjusting head and configured to take images of a surface of an object to be inspected;
   a data processor;
   a controller controlling the vertical rail and the angle adjusting head; and
   a memory,
   wherein the object to be inspected is placed on the base, and the angle adjusting head moves over the object to be inspected, the method comprising:
   (a) collecting, by the data processor, shape data of the surface of the object to be inspected from a drawing of the object designed with a computer aided design program;
   (b) calculating, by the data processor, a focal distance between each point of the surface of the object to be inspected and the image device based on the shape data, and calculating an angle of a normal line at said each point of the surface of the object based on the shape data;
   (c) inspecting the surface of the object to be inspected with moving the image device such that the angle adjusting head is located at said each point with the focal distance from said each point and a light axis of the image device is identical to the normal line at said each point,
   wherein (a) is performed prior to performing (b) and (c).

2. The method of claim 1, wherein the image device in (c) reciprocates in the vertical direction.

3. The method of claim 1, wherein the image device in (c) is operated in swing motion.

4. The method of claim 1, wherein the image device in (c) reciprocates in the vertical direction and is operated in swing motion, simultaneously.

5. A device for optically inspecting a carbon fiber reinforced plastics (CFRP) component, comprising:
   a base:
   two supports separately and vertically installed at both sides of the base;

a horizontal rail extending in a horizontal direction with a predetermined length, wherein both ends of the horizontal rail are supported by the supports;

a vertical rail extending in a vertical direction with a predetermined length and moving in the horizontal direction along the horizontal rail;

an angle adjusting head moving in the vertical direction along the vertical rail and being operated in swing motion;

an image device mounted on the angle adjusting head and configured to take images of a surface of an object to be inspected;

a data processor collecting shape data of the surface of the object to be inspected from a drawing of the object designed with a computer aided design program, calculate a focal distance between each point of the surface of the object to be inspected and the image device based on the shape data, calculate an angle of a normal line at said each point of the surface of the object based on the shape data;

a controller controlling the horizontal rail, the vertical rail and the angle adjusting head to inspect the surface of the object such that the angle adjusting head is located at said each point with the focal distance from said each point and a light axis of the image device is identical to the normal line at said each point; and a memory storing the shape data collected by the data processor, wherein the object to be inspected is placed on the base, and the angle adjusting head moves over the object to be inspected.

6. The device of claim 5, wherein the data processor collects the shape data of the surface of the object to be inspected that is oriented toward the image device.

7. The device of claim 5, wherein the vertical rail and the angle adjusting head are configured to be simultaneously operated.

* * * * *